US007928271B2

(12) United States Patent
Sievert

(10) Patent No.: US 7,928,271 B2
(45) Date of Patent: Apr. 19, 2011

(54) PROCESS FOR PRODUCING 1,2,3,3,3-PENTAFLUOROPROPENE AND RELATED AZEOTROPIC COMPOSITIONS

(75) Inventor: Allen Capron Sievert, Elkton, MD (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 228 days.

(21) Appl. No.: 12/377,776

(22) PCT Filed: Sep. 5, 2007

(86) PCT No.: PCT/US2007/019319
§ 371 (c)(1),
(2), (4) Date: Feb. 17, 2009

(87) PCT Pub. No.: WO2008/030444
PCT Pub. Date: Mar. 13, 2008

(65) Prior Publication Data
US 2010/0294979 A1       Nov. 25, 2010

Related U.S. Application Data

(60) Provisional application No. 60/842,708, filed on Sep. 5, 2006.

(51) Int. Cl.
*C07C 19/08* (2006.01)
*C07C 17/383* (2006.01)
(52) U.S. Cl. ...................................................... 570/124
(58) Field of Classification Search .................. 570/124
See application file for complete search history.

(56) References Cited

U.S. PATENT DOCUMENTS

| 4,582,570 | A |   | 4/1986  | Mix              |         |
|-----------|---|---|---------|------------------|---------|
| 4,851,595 | A |   | 7/1989  | Gumprecht        |         |
| 5,264,639 | A | * | 11/1993 | Morikawa et al.  | 570/168 |
| 5,396,000 | A |   | 3/1995  | Nappa et al.     |         |
| 5,523,501 | A |   | 6/1996  | Kellner et al.   |         |
| 2006/0106263 | A1 |   | 5/2006  | Miller et al. |         |
| 2010/0025620 | A1 | * | 2/2010  | Nappa et al. | 252/67  |
| 2010/0121115 | A1 | * | 5/2010  | Rao et al.   | 570/136 |

FOREIGN PATENT DOCUMENTS

| WO | WO 2005/012214 | * | 2/2005 |
|----|----------------|---|--------|
| WO | 2005/058489    |   | 6/2005 |
| WO | 2008030439     |   | 3/2008 |
| WO | 2008030441     |   | 3/2008 |
| WO | 2008054779     |   | 5/2008 |
| WO | 2008054780     |   | 5/2008 |

* cited by examiner

Primary Examiner — John R Hardee

(57) ABSTRACT

A process for making $CHF\!\!=\!\!CFCF_3$ is disclosed. The process involves (a) reacting $CCl_2FCF_2CF_3$ with $H_2$ in the presence of a catalytically effective amount of hydrogenation catalyst to form $CH_2FCF_2CF_3$; and (b) dehydrofluorinating $CH_2FCF_2CF_3$ from (a) to form $CHF\!\!=\!\!CFCF_3$.
Also disclosed are compositions including $CCl_3CF_2CF_3$ and HF, wherein the HF is present in an effective amount to form an azeotropic combination with the $CCl_3CF_2CF_3$; and compositions including $CCl_2FCF_2CF_3$ and HF, wherein the HF is present in an effective amount to form an azeotropic combination with the $CCl_2FCF_2CF_3$.

5 Claims, No Drawings

PROCESS FOR PRODUCING 1,2,3,3,3-PENTAFLUOROPROPENE AND RELATED AZEOTROPIC COMPOSITIONS

FIELD OF THE INVENTION

The present invention relates to a process that involves the production of halogenated hydrocarbon products comprising 1,2,3,3,3-pentafluoropropene and to related azeotropic compositions comprising hydrogen fluoride.

BACKGROUND OF THE INVENTION

As a result of the Montreal Protocol phasing out ozone depleting chlorofluorocarbons (CFCs) and hydrochlorofluorocarbons (HCFCs), industry has been working for the past few decades to find replacement refrigerants. The solution for most refrigerant producers has been the commercialization of hydrofluorocarbon (HFC) refrigerants. The new hydrofluorocarbon refrigerants, HFC-134a being the most widely used at this time, have zero ozone depletion potential and thus are not affected by the current regulatory phase out as a result of the Montreal Protocol. The production of other hydrofluorocarbons for use in applications such as solvents, blowing agents, cleaning agents, aerosol propellants, heat transfer media, dielectrics, fire extinguishants and power cycle working fluids has also been the subject of considerable interest.

There is also considerable interest in developing new refrigerants with reduced global warming potential for the mobile air-conditioning market.

HFC-1225ye, having zero ozone depletion and a low global warming potential, has been identified as a potential refrigerant. U.S. Pat. No. 5,396,000 discloses a process for producing HFC-1225ye by dehydrofluorination of $CF_3CFHCF_2H$ (HFC-236ea). There is a need for new manufacturing processes for the production of HFC-1225ye.

SUMMARY OF THE INVENTION

The present invention provides a process for making $CHF=CFCF_3$ (HFC-1225ye). This process comprises (a) reacting CFC-216cb with $H_2$ in the presence of a catalytically effective amount of hydrogenation catalyst to form $CH_2FCF_2CF_3$ (HFC-236cb); and (b) dehydrofluorinating HFC-236cb from (a) to form HFC-1225ye.

The present invention also provides a composition comprising (a) $CCl_3CF_2CF_3$ and (b) HF; wherein the HF is present in an effective amount to form an azeotropic combination with the $CCl_3CF_2CF_3$.

The present invention also provides a composition comprising (a) $CCl_2FCF_2CF_3$ and (b) HF; wherein the HF is present in an effective amount to form an azeotropic combination with the $CCl_2FCF_2CF_3$.

DETAILED DESCRIPTION

The present invention provides a process for making HFC-1225ye by a process comprising (a) reacting CFC-216cb with $H_2$ in the presence of a catalytically effective amount of hydrogenation catalyst to form $CH_2FCF_2CF_3$ (HFC-236cb); and (b) dehydrofluorinating HFC-236cb from (a) to form HFC-1225ye HFC-1225ye may exist as one of two configurational isomers, E or Z. HFC-1225ye as used herein refers to the isomers, E—HFC-1225ye (CAS Reg No. [5595-10-8]) or Z—HFC-1225ye (CAS Reg. No. [5528-43-8]), as well as any combinations or mixtures of such isomers.

CFC-216cb can be prepared from a variety of starting materials. For example, CFC-216cb can be prepared by the reaction of dichlorodifluoromethane with tetrafluoroethylene in the presence of aluminum chlorofluoride as disclosed by Sievert, et. al. in U.S. Pat. No. 5,488,189. CFC-216cb may also be prepared by fluorination of CFC-215cb ($CCl_3C_2F_5$). CFC-215cb can be prepared by the reaction of trichlorofluoromethane with tetrafluoroethylene in the presence of aluminum chloride as reported by Paleta, et. al. in Collections of Czechoslovia Chemical Communications, Vol. 36, pages 1867 to 1875 (1971).

In step (a) of the process of the invention, CFC-216cb is reacted with hydrogen in the presence of a hydrogenation catalyst. Hydrogenation catalysts suitable for use in this invention include catalysts comprising at least one catalytic metal component selected from the group consisting of rhenium, iron, ruthenium, osmium, cobalt, rhodium, iridium, nickel, palladium, and platinum. Said catalytic metal component is typically supported on a carrier such as carbon or graphite or a metal oxide, fluorinated metal oxide, or metal fluoride where the carrier metal is selected from the group consisting of magnesium, aluminum, titanium, vanadium, chromium, iron, and lanthanum.

Of note are carbon-supported catalysts in which the carbon support has been washed with acid and has an ash content below about 0.1% by weight. Hydrogenation catalysts supported on low ash carbon are described in U.S. Pat. No. 5,136,113, the teachings of which are incorporated herein by reference. Of particular note are palladium catalysts supported on carbon (see e.g., U.S. Pat. No. 5,523,501, the teachings of which are incorporated herein by reference).

The relative amount of hydrogen contacted with CFC-216cb is typically from about one mole of hydrogen per mole of CFC-216cb to about 15 moles of $H_2$ per mole of the CFC-216cb starting material, preferably from about 2 moles of hydrogen per mole of CFC-216cb to about 8 moles of $H_2$ per mole of the CFC-216cb starting material. Suitable reaction temperatures are typically from about 100° C. to about 350° C., preferably from about 125° C. to about 300° C. The contact time is typically from about 1 to about 450 seconds, preferably from about 10 to about 120 seconds. The reactions are typically conducted at atmospheric pressure or superatmospheric pressure.

The reaction of CFC-216cb with hydrogen may be carried out in the liquid phase in a reaction vessel such as an autoclave. The reaction may also be carried out in the vapor phase in a reaction vessel such as a tubular reactor.

The effluent from the reaction zone typically includes HCl, unreacted hydrogen, HFC-236cb, and one or more of CFC-216cb and HCFC-226ca ($CHClC_2F_5$). In one embodiment of the invention, the HFC-236cb is isolated by separation processes known in the art such as distillation. The isolated HFC-236cb is then used for step (b) of the process. Unreacted CFC-216cb and intermediate products such as HCFC-226ca may be recycled to step (a) of the process. In one embodiment of the process of the invention, the effluent from the reaction zone of step (a) is sent directly to step (b).

In step (b) of the process of the invention, the HFC-236cb produced in step (a) is contacted with a dehydrofluorination catalyst in a reaction zone for time sufficient to convert at least a portion of the 236cb to HFC-1225ye. Suitable dehydrofluorination catalysts include chromium oxide (e.g., $Cr_2O_3$) and chromium oxyfluorides obtained by treating $Cr_2O_3$ with a fluorinating agent such as HF or $CCl_3F$. Suitable chromium oxide may be obtained commercially. The dehydrofluorination reaction may be conducted in a tubular reactor in the vapor phase at temperatures of from about 200° C. to about 500° C. The reaction pressures may be subatmospheric, atmospheric, or superatmospheric. Contact times on the catalyst are typically in the range of about one second to 1000 seconds (e.g., about 1 second to about 120 seconds). Further details of this process are disclosed in U.S. Patent Application No. 60/830,939 filed Jul. 13, 2006, the teachings of which are incorporated by reference.

In another embodiment of this invention, the HFC-236cb is contacted with a base as disclosed in U.S. Patent Application No. 60/842,425 filed Sep. 5, 2006 (the teachings of which are incorporated by reference). U.S. Patent Application No. 60/842,425 is the priority document for International Patent Application No. PCT/US2007/019314.

Of note are embodiments where HFC-1225ye is a desired product, and is recovered from the product mixture. The HFC-1225ye present in the effluent from the reaction zone may be separated from the other components of the product mixture and unreacted starting materials by conventional means (e.g., distillation). When HF is present in the effluent, this separation can also include isolation of azeotrope or near azeotrope composition of HFC-1225ye and HF and further processing to produce HF-free HFC-1225ye by using procedures similar to that disclosed in U.S. Patent Publication US 2006/0106263 A1, which is incorporated herein by reference.

In accordance with the present invention, the CFC-216cb used as a reactant may be produced by reacting CFC-215cb with hydrogen fluoride. It is desirable to avoid production of large amounts of overfluorination products, such as CFC-217ca ($CF_3CF_2CClF_2$) and FC-218 ($CF_3CF_2CF_3$). Accordingly, the molar ratio of HF to CFC-215cb used for the partial hydrofluorination is about 1.5 or less (e.g., from about 0.5:1 to 1:1).

This partial hydrofluorination may be carried out in batch, semi-continuous, or continuous modes. In the batch mode, liquid CFC-215cb and hydrogen fluoride are combined in an autoclave or other suitable reaction vessel and heated to the desired temperature. Preferably, the process of the invention is carried out by feeding HF to a reactor containing liquid CFC-215cb held at the desired reaction temperature. Alternatively, HF may be fed to a reactor containing CFC-215cb.

In another embodiment of this partial hydrofluorination, both HF and CFC-215cb may be fed concurrently in the desired stoichiometric ratio (about 1:1) to a reactor containing CFC-215cb, CFC-216cb, or a mixture of thereof.

In yet another embodiment, CFC-215cb and HF may be fed either concurrently or separately in the desired stoichiometric ratio to a heated tubular reactor. The reactor may be empty or preferably filled with a suitable packing such as Monel® nickel alloy turnings or wool, Hastelloy® nickel alloy turnings or wool, or other material which allows efficient mixing of liquid CFC-215cb with hydrogen fluoride vapor. In one embodiment said tubular reactor is preferably oriented vertically with CFC-215cb liquid entering the top of the reactor and pre-heated HF vapor introduced at the bottom of the reactor. The CFC-215cb feed rate is determined by the length and diameter of the reactor, the temperature, and the degree of fluorination desired. Slower feed rates at a given temperature will increase contact time and tend to increase the fluorine content of the products.

Temperatures suitable for reacting CFC-215cb with HF are typically from about 30° C. to about 150° C. in liquid phase embodiments and from about 100° C. to about 250° C. in vapor phase embodiments. Higher temperatures typically result in higher conversions of CFC-215cb, but can result in reduced selectivity due to overfluorination.

The pressure of the step in which HF and CFC-215cb are contacted is not critical and in batch reactions is usually taken to be the autogenous pressure of the system at the reaction temperature. The pressure of the system increases as hydrogen chloride is formed by replacement of chlorine substituents for fluorine substituents in the CFC-215cb starting material. In a continuous process it is possible to set the pressure of the reactor in such a way that the HCl liberated by the reaction is vented from the reactor. Of note are embodiments in which both HCl and the azeotrope of HF and CFC-216cb are vented continuously from the reactor.

Of note are embodiments wherein CFC-215cb and/or CFC-216cb are present in the product mixture, and wherein said CFC-215cb and CFC-216cb are recovered. When CFC-215cb and CFC-216cb are present in the effluent from the reaction zone, they may also be separated from the other components of the product mixture by conventional means (e.g., distillation). CFC-215cb recovered from the reaction zone may be advantageously recycled thereto. When HF is present in the effluent, this separation can also include isolation of the azeotropes or near azeotropes of CFC-215cb and CFC-216cb and HF and further processing to produce HF-free CFC-215cb and CFC-216cb by using procedures similar to those disclosed in U.S. Pat. No. 6,540,933. Of note are embodiments wherein HF is fed to the reaction zone and CFC-215cb and/or CFC-216cb are present in the product mixture, and wherein at least a portion of CFC-215cb and/or CFC-216cb are recovered from the product mixture as azeotropes comprising HF and CFC-215cb and/or CFC-216cb. The HF/CFC-215cb azeotrope and near azeotrope compositions in the effluent from the partial fluorination reaction zone can be advantageously recycled back to the reaction zone and are useful in processes to produce CFC-216cb, HFC-236cb, and HFC-1225ye. The CFC-216cb/HF azeotrope may be recovered and sent to step (a), preferably after removal of the HF component of the azeotrope or can be used for further fluorination reactions (e.g., producing CFC-217ca ($CF_3CF_2CClF_2$)). Of note are embodiments where the CFC-216cb/HF azeotrope is co-fed along with hydrogen and preferably additional CFC-216cb to the reaction zone of step (a).

A catalyst is not needed for the partial hydrofluorination of CFC-215cb, but may be added if desired to increase the conversion of CFC-215cb or the rate of the reaction. Suitable catalysts which may be used for the partial hydrofluorination when carried out in the liquid phase include carbon, $AlF_3$, $BF_3$, $FeX_3$ where X is selected from the group consisting of Cl and F, $FeX_3$ supported on carbon, $SbCl_{3-x}F_x$ (x=0 to 3), $AsF_3$, $MCl_{5-y}F_y$ (M=Sb, Nb, Ta, Mo; x=0 to 5), $M'Cl_{4-z}F_z$ (M'=Sn, Ti, Zr, Hf; z=0 to 4).

Suitable catalyst which may be used for the partial hydrofluorination of CFC-215cb when carried out in the vapor phase include metals (including elemental metals, metal oxides and/or other metal salts); alumina; fluorided alumina; aluminum fluoride; metals on alumina; metals on aluminum fluoride; magnesium fluoride on aluminum fluoride; metals on fluorided alumina; alumina on carbon; aluminum fluoride on carbon; fluorided alumina on carbon; metals on carbon; chromium catalysts (e.g., $Cr_2O_3$ by itself or with other metals such as Mg, Zn, Fe, Co, Ni, Cu); mixtures of metals, aluminum fluoride, and graphite; and chromium-magnesium optionally on graphite.

Fluorided alumina and aluminum fluoride can be prepared as described in U.S. Pat. No. 4,902,838. Metals on aluminum fluoride and metals on fluorided alumina can be prepared by procedures described in U.S. Pat. No. 4,766,260. Catalysts comprising chromium are well known in the art (see e.g., U.S. Pat. No. 5,036,036). Chromium supported on alumina can be prepared as described in U.S. Pat. No. 3,541,165. Chromium supported on carbon can be prepared as described in U.S. Pat.

No. 3,632,834. Catalysts comprising chromium and magnesium may be prepared as described in U.S. Pat. No. 6,288,293. Other metals and magnesium optionally on graphite can be prepared in a similar manner to the latter patent.

The partial fluorination of CFC-215cb to CFC-216cb may also be carried out in the absence of HF using fluorination agents known in the art such as antimony trifluoride, $SbF_{5-a}X_a$ (where X=Cl or Br and a=1-4), mixtures formed by the reaction of antimony trifluoride with chlorine or bromine, or antimony pentafluoride. Such fluorinations are discussed by Hudlicky in Chemistry of Organic Fluorine Compounds, published by The MacMillan Company (New York), 1962, pages 93 to 98.

The present invention also provides azeotrope or near azeotrope compositions comprising an effective amount of hydrogen fluoride combined with a compound selected from CFC-215cb and CFC-216cb.

In connection with developing processes for the separation of the individual compounds from the reaction zone effluent from the reaction of CFC-215cb with hydrogen fluoride, it is noted that CFC-215cb and CFC-216cb (as well as HFC-1225ye and HFC-236cb) each can be present as their respective azeotrope or near azeotrope with HF. HF may be present as unreacted starting material from the partial fluorination of CFC-215cb or from the dehydrofluorination reactions of HFC-236cb (or intermediates containing six fluorines to compounds containing at least one less fluorine), from hydrodefluorination side reactions, or from HF co-fed along with hydrogen to the reaction zone of step (a).

By effective amount is meant an amount, which, when combined with CFC-216cbb or CFC-215cb, results in the formation of their respective azeotrope or near azeotrope mixture. As recognized in the art, an azeotrope or a near azeotrope composition is an admixture of two or more different components which, when in liquid form under a given pressure, will boil at a substantially constant temperature, which temperature may be higher or lower than the boiling temperatures of the individual components, and which will provide a vapor composition essentially identical to the liquid composition undergoing boiling.

For the purpose of this discussion, near azeotrope composition (also commonly referred to as an "azeotrope-like composition") means a composition that behaves like an azeotrope (i.e., has constant boiling characteristics or a tendency not to fractionate upon boiling or evaporation). Thus, the composition of the vapor formed during boiling or evaporation is the same as or substantially the same as the original liquid composition. Hence, during boiling or evaporation, the liquid composition, if it changes at all, changes only to a minimal or negligible extent. This is to be contrasted with non-near azeotrope compositions in which during boiling or evaporation, the liquid composition changes to a substantial degree.

Additionally, near azeotrope compositions exhibit dew point pressure and bubble point pressure with virtually no pressure differential. That is to say that the difference in the dew point pressure and bubble point pressure at a given temperature will be a small value. In this invention, compositions with a difference in dew point pressure and bubble point pressure of less than or equal to 3 percent (based upon the bubble point pressure) are considered to be near azeotropes.

Accordingly, the essential features of an azeotrope or a near azeotrope composition are that at a given pressure, the boiling point of the liquid composition is fixed and that the composition of the vapor above the boiling composition is essentially that of the boiling liquid composition (i.e., no fractionation of the components of the liquid composition takes place). It is also recognized in the art that both the boiling point and the weight percentages of each component of the azeotrope composition may change when the azeotrope or near azeotrope liquid composition is subjected to boiling at different pressures. Thus, an azeotrope or a near azeotrope composition may be defined in terms of the unique relationship that exists among the components or in terms of the compositional ranges of the components or in terms of exact weight percentages of each component of the composition characterized by a fixed boiling point at a specified pressure. It is also recognized in the art that various azeotrope compositions (including their boiling points at particular pressures) may be calculated (see, e.g., W. Schotte Ind. Eng. Chem. Process Des. Dev. (1980) 19, 432-439). Experimental identification of azeotrope compositions involving the same components may be used to confirm the accuracy of such calculations and/or to modify the calculations at the same or other temperatures and pressures.

In accordance with this invention, compositions are provided which comprise CFC-215cb and HF wherein HF is present in an effective amount to form an azeotropic combination with the CFC-215cb. According to calculations, CFC-215cb and HF form a heterogeneous azeotrope. A heterogeneous azeotrope differs from a homogeneous azeotrope in that a heterogeneous azeotrope composition comprises two distinct liquid phases in equilibrium with a vapor phase. Either of the two liquid phases may have a composition that is quite different from the other liquid phase. The overall composition of the liquid phases may be said to comprise a weighted average of the separate liquid phase compositions and that overall composition of the liquid phases will be substantially the same as the vapor phase composition at the azeotrope point for a given temperature and pressure. The azeotropic mixture of CFC-215cb and HF or CFC-216cb and HF may be directed to a phase separation device such as a decanter for isolation of HF-rich and organic-rich phases.

Calculations of the azeotrope for CFC-215cb and HF have provided overall compositions comprising from about 84.7 mole percent to about 98.6 mole percent HF and from about 15.3 mole percent to about 1.4 mole percent CFC-215cb (which form azeotropes boiling at a temperature of from about −30° C. to about 120° C. and at a pressure of from about 1.8 psi (12.4 kPa) to about 327 psi (2255 kPa)). Subsequent to these calculations, an azeotrope of about 95.2 mole percent HF and 4.8 mole percent CFC-215cb boiling at a temperature of about 34.7° C. at a pressure of 28.0 psi (193 kPa), and an azeotrope of about 91.4 mole percent HF and 8.6 mole percent CFC-215cb boiling at a temperature of about 84.6° C. at a pressure of 126 psi (689 kPa) were found. Additional calculations in light of these findings, provided overall compositions comprising from about 89.1 mole percent to about 98.1 mole percent HF and from about 10.9 mole percent to about 1.9 mole percent CFC-215cb (which form azeotropes boiling at a temperature of from about −20° C. to about 110° C. and at a pressure of from about 3.0 psi (20.7 kPa) to about 240 psi (1655 kPa)). In accordance with this invention, compositions are provided which comprise CFC-216cb and HF wherein HF is present in an effective amount to form an azeotropic combination with the CFC-216cb. According to calculations, CFC-216cb and HF also form a heterogeneous azeotrope. Calculations of the azeotrope for CFC-216cb and HF have provided overall compositions comprising from about 73.1 mole percent to about 90.4 mole percent HF and from about 26.9 mole percent to about 9.6 mole percent CFC-216cb (which form azeotropes boiling at a temperature of from about −30° C. to about 120° C. and at a pressure of from about 2.4 psi (16.5 kPa) to about 420 psi (2896 kPa)).

The reactor, distillation columns, and their associated feed lines, effluent lines, and associated units used in applying the processes of this invention should be constructed of materials resistant to hydrogen fluoride and hydrogen chloride. Typical materials of construction, well-known to the fluorination art, include stainless steels, in particular of the austenitic type, the well-known high nickel alloys, such as Monel™ nickel-copper alloys, Hastelloy™ nickel-based alloys and, Inconel™ nickel-chromium alloys, and copper-clad steel.

The following specific Examples are to be construed as merely illustrative, and do not constrain the remainder of the disclosure in any way whatsoever.

EXAMPLES

Legend

| | |
|---|---|
| CFC-216cb | $CCl_2FC_2F_5$ |
| HCFC-226ca | $CHClFC_2F_5$ |
| HFC-236cb | $CH_2FC_2F_5$ |
| HFC-236ea | $CHF_2CHCF_3$ |
| Z-HFC-1225ye | $Z\text{-}CHF\!=\!CFCF_3$ |
| E-HFC-1225ye | $E\text{-}CHF\!=\!CFCF_3$ |

Example 1

Hydrodechlorination of CFC-216cb

Hydrodechlorination of CFC-216cb is illustrated by the following prophetic example based largely on the teachings of U.S. Pat. No. 5,523,501, incorporated herein by reference. CFC-216cb may be converted to HFC-236cb by reaction of hydrogen over a palladium catalyst.

A 2 weight percent palladium supported on acid-washed carbon catalyst (46 g, 4-8 mesh (4.7-2.4 mm)) is placed in a 33 cm×2.54 cm o.d. Hastelloy® tube. The tube is connected to a reactor system and surrounded with an electrically-heated furnace. The catalyst is activated by drying at 150° C. for several hours under a nitrogen purge (100 sccm, $1.7 \times 10^{-6}$ m³/s) followed by treatment with 1:1 nitrogen:hydrogen (100 sccm, $1.7 \times 10^{-6}$ m³/s each) for 5 hours at 150° C. Finally, the catalyst is treated with hydrogen gas (100 sccm, $1.7 \times 10^{-6}$ m³/s) at 275° C. for an additional two hours. The flow of hydrogen is then replaced with nitrogen (100 sccm, $1.7 \times 10^{-6}$ m³/s) as the temperature is reduced to 150° C. A mixture of CFC-216cb (52 sccm, $8.8 \times 10^{-7}$ m³/s) and hydrogen (300 sccm, $5.1 \times 10^{-6}$ m³/s) is passed through the catalyst bed at 150° C. Under these conditions the conversion of CFC-216cb is essentially complete and the reactor effluent is a mixture of approximately 3:1 HFC-236cb:HCFC-226ca.

Example 2

Dehydrofluorination of HFC-236cb

Dehydrofluorination of HFC-236cb is illustrated by the following prophetic example based largely on the teachings of U.S. Patent Application No. 60/830,939, filed Jul. 13, 2006 and International Application No. PCT/US2007/015751, filed Jul. 11, 2007, both incorporated herein by reference.

An Inconel™ tube (⅝ inch OD (1.59 cm)) is charged with chromium oxide pellets (5 cc, 7.18 g, 12-20 mesh (1.68-0.84 mm)). The chromium oxide is prepared by the pyrolysis of ammonium dichromate as described in U.S. Pat. No. 5,036,036, herein incorporated by reference. The chromium oxide has an alpha-$Cr_2O_3$ structure and contains less than about 100 ppm of alkali metals; the surface area is about 40-60 m²/gm. The chromium oxide is activated according to the following sequence: (1) heating to 200° C. for 15 minutes under a purge of $N_2$ (50 sccm, $8.33 \times 10^{-7}$ m³/s) and then increasing the temperature to 400° C. over 30 minutes, (2) lowering the temperature to 300° C. for 35 minutes, (3) flowing $N_2$ (35 sccm, $5.83 \times 10^{-7}$ m³/s) and HF (12 sccm, $2.00 \times 10^{-7}$ m³/s) for 35 minutes and then increasing the temperature to 350° C. for 60 minutes, followed by 375° C. for 90 minutes, followed by 400° C. for 30 minutes, and finally 425° C. for 40 minutes, (4) while maintaining the temperature at 425° C., the flow of $N_2$ is reduced to 25 sccm ($4.17 \times 10^{-7}$ m³/s) and HF is increased to 20 sccm ($3.33 \times 10^{-7}$ m³/s) for 20 minutes, (5) while maintaining the temperature at 425° C., the flow of $N_2$ is reduced to 15 sccm ($2.50 \times 10^{-7}$ m³/s) and HF is increased to 28 sccm ($4.67 \times 10^{-7}$ m³/s) for 20 minutes, (6) while maintaining the temperature at 425° C., the flow of $N_2$ is reduced to 5 sccm ($8.33 \times 10^{-8}$ m³/s) and HF is increased to 36 sccm ($6.00 \times 10^{-7}$ m³/s) for 20 minutes. The flow of HF is then stopped and the reactor tube cooled to about 350° C. under a nitrogen flow. HFC-236cb and nitrogen are then passed through the catalyst bed at about 21 sccm ($3.5 \times 10^{-7}$ m³/s) and 5.0 sccm ($8.33 \times 10^8$ m³/s), respectively; contact time of the HFC-236cb with the catalyst is about 30 seconds. Analysis of the reactor effluent shows approximately 60 GC area % HFC-236cb, 32 GC area % Z—HFC-1225ye, 4 GC area % E—HFC-1225ye, and 4 GC area % HFC-236ea.

What is claimed is:

1. A composition comprising:
    (a) $CCl_3CF_2CF_3$; and
    (b) HF; wherein the HF is present in an effective amount to form an azeotropic combination with the $CCl_3CF_2CF_3$.

2. The composition of claim 1 comprising from about 1.4 mole percent to about 15.3 mole percent $CCl_3CF_2CF_3$ and hydrogen fluoride.

3. The composition of claim 2, comprising from about 1.4 mole percent to about 15.3 mole percent $CCl_3CF_2CF_3$ and hydrogen fluoride, having a vapor pressure of from about 1.8 psi to about 327 psi, at to temperature of from about −30° C. to about 120° C.

4. The composition of claim 1, comprising from about 1.9 mole percent to about 10.9 mole percent $CCl_3CF_2CF_3$ and hydrogen fluoride.

5. The composition of claim 4, comprising from about 1.9 mole percent to about 10.9 mole percent $CCl_3CF_2CF_3$ and hydrogen fluoride, having a vapor pressure of from about 3.0 psi to about 240 psi, at a temperature for from about −20° C. to about 110° C.

\* \* \* \* \*